US012329831B2

(12) United States Patent
Tafti

(10) Patent No.: US 12,329,831 B2
(45) Date of Patent: Jun. 17, 2025

(54) RADIONUCLIDE-LOADED NANOPARTICLES FOR FOCAL TISSUE ABLATION

(71) Applicant: Translational and Fundamental Technologies Institute LLC, Encino, CA (US)

(72) Inventor: Bashir Akhavan Tafti, Encino, CA (US)

(73) Assignee: TRANSLATIONAL AND FUNDAMENTAL TECHNOLOGIES INSTITUTE LLC, Encino, CA (US)

( * ) Notice: Subject to any disclaimer, the term of this patent is extended or adjusted under 35 U.S.C. 154(b) by 0 days.

(21) Appl. No.: 18/609,663

(22) Filed: Mar. 19, 2024

(65) Prior Publication Data

US 2024/0350684 A1    Oct. 24, 2024

Related U.S. Application Data

(60) Provisional application No. 63/461,297, filed on Apr. 23, 2023.

(51) Int. Cl.
*A61K 51/12*    (2006.01)
*A61K 51/04*    (2006.01)
(Continued)

(52) U.S. Cl.
CPC ...... *A61K 51/1251* (2013.01); *A61K 51/0497* (2013.01); *A61K 51/088* (2013.01);
(Continued)

(58) Field of Classification Search
None
See application file for complete search history.

(56) References Cited

U.S. PATENT DOCUMENTS 6,818,199 B1    11/2004 Hainfeld et al.
9,433,392 B2    9/2016 Ohishi
(Continued)

FOREIGN PATENT DOCUMENTS

EP    2331064 A1    6/2011
KR    20180010222 A  *  1/2018
(Continued)

OTHER PUBLICATIONS

Wikimedia Foundation. (Jan. 15, 2016). Microparticle. Wikipedia. https://en.wikipedia.org/wiki/Microparticle (Year: 2016).*
(Continued)

*Primary Examiner* — Carrie R Dorna
*Assistant Examiner* — Marc D. Honrath
(74) *Attorney, Agent, or Firm* — Clark & Elbing LLP

(57) ABSTRACT

The present disclosure features radiopharmaceutical compositions including a radionuclide and an imaging agent encapsulated within, embedded in, or conjugated to a nanoparticle (e.g., via a complexing moiety, such as a chelator), and methods of their use. The radiopharmaceuticals may be formulated for direct administration to the diseased tissue, with minimal or no washout of the radiopharmaceutical to non-target sites within a subject. The radiopharmaceuticals of the present disclosure allow for efficient treatment of diseased tissue proximal to the site of administration with minimal to no damage to the surrounding tissue.

28 Claims, 2 Drawing Sheets

TAT

(51) Int. Cl.
  *A61K 51/08* (2006.01)
  *A61N 5/10* (2006.01)
  *A61P 35/00* (2006.01)
(52) U.S. Cl.
  CPC ............ *A61N 5/1002* (2013.01); *A61P 35/00* (2018.01); *A61N 2005/1021* (2013.01); *A61N 2005/1087* (2013.01)

(56) References Cited

U.S. PATENT DOCUMENTS

| | | | |
|---|---|---|---|
| 9,597,419 B2 | 3/2017 | Fritz et al. | |
| 9,694,742 B2 | 7/2017 | Newbound et al. | |
| 9,738,596 B2 | 8/2017 | Thaning | |
| 10,058,633 B2 | 8/2018 | Ferrari et al. | |
| 11,207,104 B2 | 12/2021 | Mullaney et al. | |
| 11,712,487 B2 | 8/2023 | Tafti | |
| 2003/0120355 A1 | 6/2003 | Hafeli et al. | |
| 2004/0022840 A1* | 2/2004 | Nagy | A61K 9/1273 424/185.1 |
| 2007/0031327 A1* | 2/2007 | Luzzi | B82Y 10/00 424/1.11 |
| 2009/0136422 A1* | 5/2009 | Kelson | A61P 35/00 424/1.73 |
| 2011/0176997 A1 | 7/2011 | Zhang | |
| 2011/0301452 A1 | 12/2011 | Maschke et al. | |
| 2012/0123189 A1 | 5/2012 | Ribbing et al. | |
| 2014/0193331 A1 | 7/2014 | Naczynski et al. | |
| 2015/0147276 A1 | 5/2015 | Ingber et al. | |
| 2015/0202326 A1 | 7/2015 | Ohri et al. | |
| 2015/0320895 A1* | 11/2015 | Sun | B82Y 30/00 424/1.29 |
| 2016/0038418 A1 | 2/2016 | DeSimone et al. | |
| 2016/0213793 A1 | 7/2016 | Goodman et al. | |
| 2019/0328677 A1 | 10/2019 | Kim et al. | |
| 2020/0138988 A1* | 5/2020 | Tafti | A61P 35/00 |
| 2024/0009332 A1 | 1/2024 | Tafti | |

FOREIGN PATENT DOCUMENTS

| | | |
|---|---|---|
| WO | WO-92/05866 A2 | 4/1992 |
| WO | WO-1994/014478 A1 | 7/1994 |
| WO | WO-2005/044224 A2 | 5/2005 |
| WO | WO-2009/073193 A2 | 6/2009 |
| WO | WO-2009/110939 A2 | 9/2009 |
| WO | WO-2010/015824 A1 | 2/2010 |
| WO | WO-2010/028048 A1 | 3/2010 |
| WO | WO-2010/052455 A1 | 5/2010 |
| WO | WO-2012/007456 A1 | 1/2012 |
| WO | WO-2014/030993 A1 | 2/2014 |
| WO | WO-2015/040128 A1 | 3/2015 |
| WO | WO-2015/123082 A1 | 8/2015 |
| WO | WO-2017/158093 A1 | 9/2017 |
| WO | WO-2018/200802 A1 | 11/2018 |
| WO | WO-2019/006099 A1 | 1/2019 |
| WO | WO-2021/044153 A1 | 3/2021 |

OTHER PUBLICATIONS

Zhao, J., Zhou, M., & Li, C. (2016). Synthetic nanoparticles for delivery of radioisotopes and radiosensitizers in cancer therapy. Cancer Nanotechnology, 7(1). https://doi.org/10.1186/s12645-016-0022-9 (Year: 2016).*

Gessner, I., & Neundorf, I. (2020). Nanoparticles modified with cell-penetrating peptides: Conjugation mechanisms, physicochemical properties, and application in cancer diagnosis and therapy. International Journal of Molecular Sciences, 21(7), 2536. https://doi.org/10.3390/ijms21072536 (Year: 2020).*

Seniwal, B., Thipe, V. C., Singh, S., Fonseca, T. C., & Freitas de Freitas, L. (2021). Recent advances in brachytherapy using radioactive nanoparticles: An alternative to seed-based brachytherapy. Frontiers in Oncology, 11. https://doi.org/10.3389/fonc.2021.766407 (Year: 2021).*

Guidoccio, F., & Mazzarri, S. (2022). Novel radiopharmaceuticals for therapy. Nuclear Oncology, 173-198. https://doi.org/10.1007/978-3-319-26236-9_36 (Year: 2022).*

Wikimedia Foundation. (Nov. 15, 2022). Specific activity. Wikipedia. https://en.wikipedia.org/wiki/Specific_activity (Year: 2022).*

U.S. Appl. No. 18/524,929, Tafti, Bashir Akhavan.

"Cancer Facts & Figures 2016," Atlanta: American Cancer Society (2016) (70 pages).

Ali-zade, R. A., "Investigation of polymer magnetic microspheres", Colloids and Surfaces A: Physiochemical and Engineering Aspects, 225:1-3, 111-117 (Mar. 2005) (7 pages).

Altekruse et al., "Hepatocellular Carcinoma Incidence, Mortality, and Survival Trends in the United States from 1975 to 2005," J. Clin Oncol. 27(9):1485-1491 (Mar. 2009) (7 pages).

Baio et al., "Reversible activation of pH-sensitive cell penetrating peptides attached to gold surfaces," available in PMC Oct. 6, 2015, published in final edited form as: Chem Commun (Camb). 51(2):273-275 (Oct. 2015) (9 pages).

Barth et al., "Current status of boron neutron capture therapy of high grade gliomas and recurrent head and neck cancer," Radiation Oncology. 7(146):1-21 (2012) (21 pages).

Bilbao et al., "Complications of Embolization," Semin Intervent Radial, 23(2):126-142 (2006) (17 pages).

Brechbiel, M. W., "Bifunctional chelates for metal nuclides," QJ Nucl. Med. Mol. Imaging. 52(2):166-173 (Jun. 2008) (8 pages).

Dharap et al., "Tumor-specific targeting of an anticancer drug delivery system by LHRH peptide," PNAS. 102(36):12962-12967 (Sep. 2005) (6 pages).

El-Say, K.M. and El Sawy, H.S., "Polymeric nanoparticles: Promising platform for drug delivery", International Journal of Pharmaceuticals, 528:1-2, 675-691, (Jun. 2017) (17 pages).

Gijs et al., "Microfluidic applications of magnetic particles for biological analysis and catalysis", Chemical Reviews 110:3, 1518-1563, (2010) (46 pages).

Iordache et al., "Poly(lactic-co-glycolic) acid/chitosan microsphere thin films functionalized with Cinnamomi aetheroleumand magnetite nanoparticles for preventing the microbial colonization of medical surfaces", Journal of Sol-Gel Science and Technology 73:3, 679-686 (Feb. 2015) (8 pages).

Kriegel et al., "Multi-compartmental oral delivery systems for nucleic acid therapy in the gastrointestinal tract", Advanced Drug Delivery Reviews 65:6, 891-901 (Dec. 2012) (11 pages).

Liu et al., "A Brief Review of Chelators for Radiolabeling Oligomers," Materials. 3:3204-3217 (May 2010) (14 pages).

M.F. Maitz, "Applications of synthetic polymers in clinical medicine," Biosurface and Biotribology. 1:161-176 (2015) (16 pages).

Pandori et al., "Adenovirus-Microbead Conjugates Possess Enhanced Infectivity: A New Strategy for Localized Gene Delivery," Virology 299(2):204-2012 (Apr. 2002) (9 pages).

Peers et al., "Dietary Aflatoxins and Liver Cancer—A Population Based Study in Kenya," Br. J. Cancer. 27(6):473-484 (Feb. 1973) (12 pages).

Vaidya S et al., "An overview of embolic agents," Semin Intervent Radiol. 25(3):204-15 (Sep. 2008) (12 pages).

Vroman et al., "Biodegradable Polymers," Materials. 2:307-344 (Apr. 2009) (38 pages).

Xie et al., "Nanoparticle-based theranostic agents," available in PMC Aug. 30, 2011, published in final edited form as: Adv Drug Deliv Rev. 62(11): 1064-1079 (Aug. 2010) (32 pages).

International Search Report and Written Opinion for PCT/US2024/020578, mailed Jul. 1, 2024 (15 pages).

Kim et al., "Ideal Size Range for Embolic Agents in Interventional Oncology Experiments Involving Rat Models of Hepatocellular Carcinoma," J Vasc Interv Radiol. 34(1):23-30 (Jan. 2023).

* cited by examiner

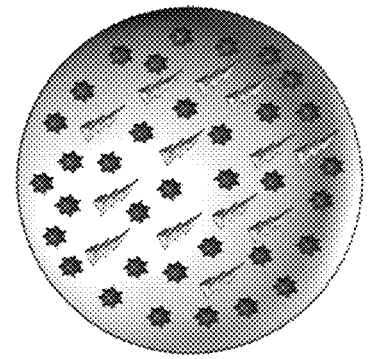
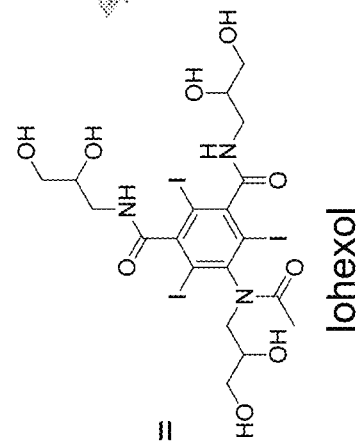
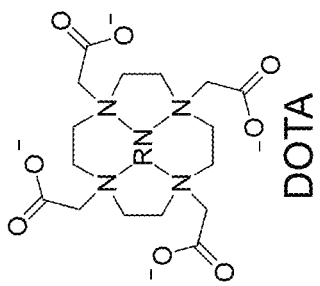
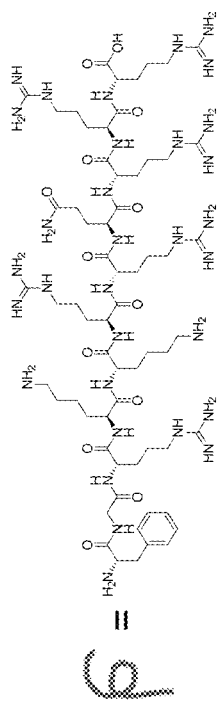
FIG. 1A
FIG. 1B

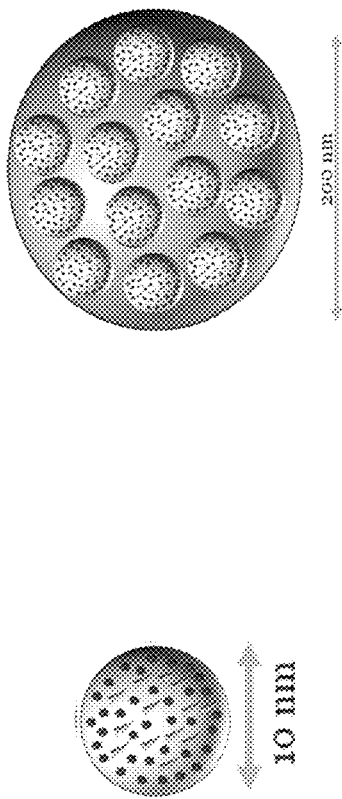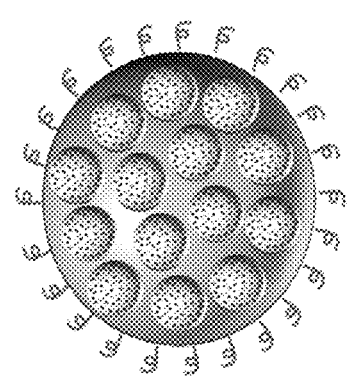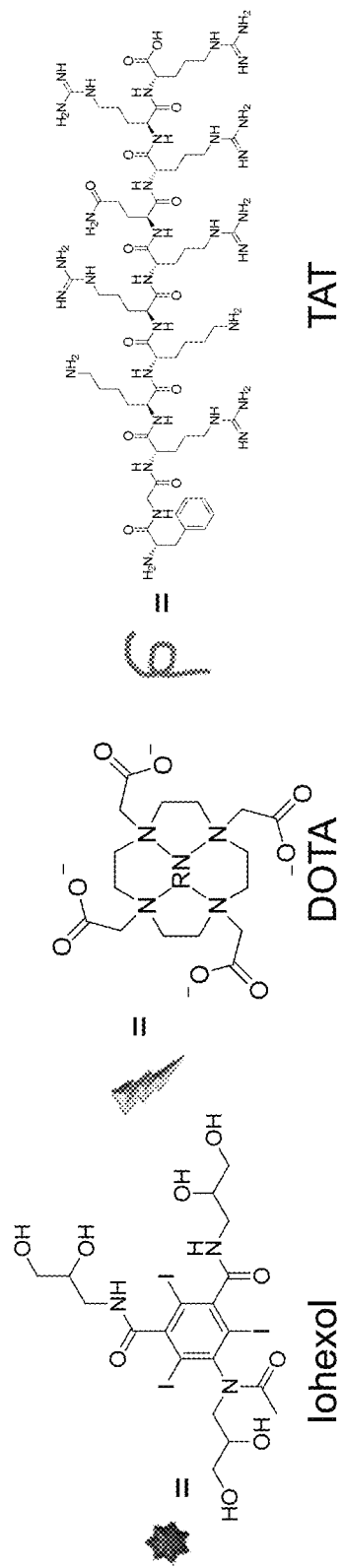

RADIONUCLIDE-LOADED NANOPARTICLES FOR FOCAL TISSUE ABLATION

BACKGROUND

Radionuclides, particularly α-emitting radionuclides, have distinct advantages for treatment of neoplastic tissues, such as malignancies. First, the very short range of α particles in soft tissue (usually less than 40 microns, equivalent to the diameter of a few human cells) allows for selective elimination of the target cells while sparing the surrounding healthy tissue. Second, α particles have higher cell-killing efficacy because they deposit significantly higher amounts of energy per unit distance compared to other ionizing particles (high linear energy transfer). Finally, in contrast to other sources of ionizing radiation, the lethal effect of α particles is based on causing double strand and cluster DNA breaks, a process that is largely independent of cell cycle and oxygenation status. Consequently, α radiation can induce apoptosis (i.e. programmed cell death) in cells that are resistant to other forms of ionizing radiation or chemotherapeutic drugs. This latter characteristic offers a therapeutic option for patients with tumors resistant to conventional therapies.

Almost all of the currently available radiopharmaceuticals based on α-emitting particles are formulated for intravenous administration. In this approach, the α-emitting radionuclides are attached to a targeting moiety with preferential binding to the target cells (e.g. antibodies, antibody fragments, or cancer-cell binding peptides). These radiopharmaceuticals are then injected into the systemic circulation through a peripheral or central vein. The problem with such pharmaceuticals is that a large portion of the injected dose will be taken up by other organs including kidneys and the liver, causing large doses of radiation to these non-target organs.

To overcome the above problem of non-target uptake and radiation, direct intratumoral injection of α-emitting radiopharmaceuticals has been suggested as an alternative route of administration. This approach comes with its own limitations. For instance, when a radionuclide is directly injected into the target tissue parenchyma, there is rapid washout of the injected material causing suboptimal dose delivery to the target cells and systemic distribution of the injected dose causing non-target radiation. Currently proposed α-emitting radiopharmaceuticals (both systemic and direct injection formulations) have several problems, including: (1) lack of intra- and postoperative visualization using conventional medical imaging modalities including ultrasound (US), fluoroscopy, computed tomography (CT), and magnetic resonance imaging (MRI); and (2) suboptimal post-treatment dosimetry. Intra- and postoperative visualization by conventional medical imaging modalities is very important for procedural planning as well as determining tissue distribution of the injected compounds at the time of administration and on follow up visits. Posttreatment dosimetry (i.e. determining the actual radiation energy deposited per unit volume of the target tissue) is very important for evaluation of safety and efficacy of the administered dose. However, the α-emitting radionuclides cannot be imaged directly due to short range of the α particles and current dosimetry techniques are based on semi-quantitative imaging of gamma rays produced during complex decay chains of the daughter radionuclides.

Accordingly, there is a need in the art for new radiation-emitting radiopharmaceuticals.

SUMMARY OF THE DISCLOSURE

The present disclosure features radiopharmaceutical compositions including a radionuclide and an imaging agent encapsulated within, embedded in, or conjugated to a nanoparticle (e.g., by a complexing moiety), and methods of their use. The radiopharmaceuticals are formulated for direct administration to the diseased tissue, with minimal or no washout of the radiopharmaceutical to non-target sites within a subject. The radiopharmaceuticals of the present disclosure allow for efficient treatment of diseased tissue proximal to the site of administration with minimal to no damage to the surrounding tissue.

In a first aspect, the disclosure features a radiopharmaceutical including: (a) a nanoparticle including or formed from a matrix with an exterior surface; (b) an imaging agent; and (c) a radionuclide bound to a chelating agent; wherein the imaging agent and the radionuclide are encapsulated within the nanoparticle. The radiopharmaceutical may also include (d) a cell-penetrating ligand, wherein the cell-penetrating ligand is conjugated to the exterior surface of the nanoparticle matrix of the radiopharmaceutical.

In some embodiments, the nanoparticle matrix includes or is formed from a polymer matrix. In some embodiments, the polymer is or includes hyaluronic acid (HA), polyethylene glycol diacrylate (PEGDA), polyglycolic acid (PGA), polylactic acid (PLA), poly(lactic-co-glycolic acid) (PLGA), polysaccharide, polycaprolactone (PCL), collagen, gelatin, poly(methyl methacrylate) (PMMA), polystyrene, carboxymethyl chitosan (CCN), carboxymethyl cellulose (CMC), phospholipids, or a combination thereof.

In some embodiments, the nanoparticle is spherical, elliptical, rod-shaped, cylindrical, prismatic, or irregular. In some embodiments, the nanoparticle is from about 1 nm to about 900 nm in diameter. In some embodiments, the nanoparticle is from about 30 nm to about 200 nm in diameter.

In some embodiments, the imaging agent can be visualized using an imaging modality, such as, e.g., by ultrasound, fluoroscopy, computed tomography, magnetic resonance imaging, single photon emission computed tomography, positron emission tomography, or a combination thereof. In some embodiments, the imaging agent includes a phospholipid, Feraheme, Gadolinium, Holmium, Europium, Thulium, Cu-64, Tc-99m, In-111, Visipaque, Iohexol or a derivative thereof, Iohexol related compound B or a derivative thereof, or a combination thereof.

In some embodiments, the radionuclide is a therapeutic radionuclide. In some embodiments, the radionuclide is an α-emitting radionuclide, a β-emitting radionuclide, or an Auger electron emitting radionuclide, in particular an α-emitting radionuclide. In some embodiments, the radionuclide undergoes radioactive decay to produce a daughter nucleus, wherein the daughter nucleus is a radionuclide (e.g., a therapeutic radionuclide). In some embodiments, the daughter nucleus is an α-emitting radionuclide, a β-emitting radionuclide, or an Auger electron emitting radionuclide. In some embodiments, the radionuclide includes terbium-149, astatine-211, bismuth-212, lead-212, bismuth-213, radium-223, radium-224, actinium-225, thorium-227, yttrium-90, iodine-131, holmium-166, lutetium-177, or a combination thereof. In preferred embodiments, the radionuclide and/or the daughter nucleus thereof is an α-emitting radionuclide.

In some embodiments, the radiopharmaceutical may further include a complexing moiety, the complexing moiety including a proximal end and a distal end, in which the complexing moiety is bound to the surface of the nanoparticle at the distal end and either the cell-penetrating ligand or a second radionuclide at the proximal end. In some embodiments, the complexing moiety is a chelator. In some embodiments, the complexing moiety is diethylenetriaminepentaacetate (DTPA), 1,4,7,10-tetraazacyclododecane-1,4,7,10-tetraacetate (DOTA), ethylenediamine tetraacetate (EDTA), cis-1,3,5-cyclohexantriamine (CHTA), triethylene glycol diamine tetraacetate (EGTA), 1,4,8,11-tetraazacyclotetradecane-1,4,8,11-tetraacetate (TETA), 1,4,7,10-tetraazacyclododecane-1,4,7-triacetate (DO3A), 1,4,7-triazacyclononane-1,4,7-triacetate (NOTA), 1,4,7,10,13,16-hexaazacyclooctadecane-1,4,7,10,13,16-hexaacetate (HEHA), N,N'-[(6-carboxy-2-pyridyl(methyl)]-4,13-diaza-18-crown-6 (MACROPA), a reactive derivative thereof, or a combination thereof. In some embodiments, the complexing moiety is chemically conjugated with the nanoparticle through a covalent bond. In some embodiments, the complexing moiety is chemically conjugated to the nanoparticle through an ionic bond.

In order to slow washout of a radiopharmaceutical composition into the vasculature of a subject, the radiopharmaceutical includes a cell-penetrating ligand, which facilitates movement of a material across a cell membrane. In some embodiments, the cell-penetrating ligand is covalently attached to the exterior surface of the nanoparticle. In some embodiments, the cell-penetrating ligand is TAT, HSV, gH625, penetratin, VP22, transportan, or a combination thereof.

In some embodiments, the radiopharmaceutical further includes a sub-nanoparticle. In some embodiments, the sub-nanoparticle is encapsulated within the nanoparticle. In some embodiments, the sub-nanoparticle includes a metal matrix. In some embodiments, the metal includes iron, gold, platinum, tantalum, an oxide thereof, or an alloy thereof. In some embodiments, the metal includes an iron oxide, wherein the iron oxide is magnetite ($Fe_3O_4$), maghemite ($\gamma$-$Fe_2O_3$), or hematite ($\alpha$-$Fe_2O_3$). In some embodiments, the sub-nanoparticle includes a polymer matrix. In some embodiments, the polymer matrix includes hyaluronic acid (HA), polyethylene glycol diacrylate (PEGDA), polyglycolic acid (PGA), polylactic acid (PLA), poly(lactic-co-glycolic acid) (PLGA), polysaccharide, polycaprolactone (PCL), Collagen, Gelatin, poly(methyl methacrylate) (PMMA), polystyrene, carboxymethyl chitosan (CCN), carboxymethyl cellulose (CMC), phospholipids, or a combination thereof. In some embodiments, the sub-nanoparticle is from about 1 nm to about 10 nm.

In some embodiments, the sub-nanoparticle further includes an imaging agent. In some embodiments, the imaging agent can be visualized by an imaging modality, such as, e.g., by ultrasound, fluoroscopy, computed tomography, magnetic resonance imaging, single photon emission computed tomography, positron emission tomography, or a combination thereof. In some embodiments, the imaging agent includes phospholipids, Feraheme, Gadolinium, Holmium, Europium, Thulium, Cu-64, Tc-99m, In-111, Visipaque, Iohexol, Iohexol related compound B or a derivative thereof, or a combination thereof. In some embodiments, the imaging agent and/or the imaging modality of the sub-nanoparticle are different from the imaging agent and/or the imaging modality of the nanoparticle.

In some embodiments, the radionuclide of the nanoparticle is localized within the sub-nanoparticle. In some embodiments, the radionuclide further includes a complexing moiety comprising a proximal end and a distal end, wherein the complexing moiety is bound to the surface of the nanoparticle at the distal end and a second radionuclide at the proximal end. In some embodiments, the complexing moiety of the sub-nanoparticle is a chelator. In some embodiments, the complexing moiety of the sub-nanoparticle is diethylenetriaminepentaacetate (DTPA), 1,4,7,10-tetraazacyclododecane-1,4,7,10-tetraacetate (DOTA), ethylenediamine tetraacetate (EDTA), cis-1,3,5-cyclohexantriamine (CHTA), triethylene glycol diamine tetraacetate (EGTA), 1,4,8,11-tetraazacyclotetradecane-1,4,8,11-tetraacetate (TETA), 1,4,7,10-tetraazacyclododecane-1,4,7-triacetate (DO3A), 1,4,7-triazacyclononane-1,4,7-triacetate (NOTA), 1,4,7,10,13,16-hexaazacyclooctadecane-1,4,7,10,13,16-hexaacetate (HEHA), N,N'-[(6-carboxy-2-pyridyl(methyl)]-4,13-diaza-18-crown-6 (MACROPA), a reactive derivative thereof, or a combination thereof.

In some embodiments, the nanoparticle and the sub-nanoparticle include an identical matrix, imaging agent, radionuclide, and/or complexing moiety.

In a second aspect, the disclosure features a pharmaceutical composition including a radiopharmaceutical of the first aspect and a pharmaceutically acceptable excipient. In some embodiments, the excipient is a polyol, a polyether, salcaprozate sodium, or sodium caprate. In some embodiments, the polyol is polyethylene glycol (PEG). In some embodiments, the activity of the radionuclide in the nanoparticle is at least 0.25 kBq per mL of the pharmaceutical composition (e.g., at the time of administration to a subject). In some embodiments, the radionuclide is a therapeutic radionuclide, wherein the specific activity of the therapeutic radionuclide of the radiopharmaceutical is from about 0.01 µBq per radiopharmaceutical to about 10 µBq per radiopharmaceutical. In some embodiments, the radionuclide is a therapeutic radionuclide, wherein the specific activity of the therapeutic radionuclide of the radiopharmaceutical is from about 0.05 µBq per radiopharmaceutical to about 2 µBq per radiopharmaceutical.

In a third aspect, the disclosure features a kit including a radiopharmaceutical of the first aspect or the pharmaceutical composition of the second aspect. In some embodiments, the kit further includes a mixer. In some embodiments, the kit further includes a delivery device. In some embodiments, the delivery device includes a puncture set for providing vascular access (e.g., a vascular access micro puncture set and access sheath).

In a fourth aspect, the disclosure features a method of treating, detecting, or visualizing a disease in a subject, including administering the radiopharmaceutical of the first aspect, or the pharmaceutical composition of the second aspect to a subject in need thereof.

In some embodiments, the disease includes neoplastic tissue (e.g., a cancer). In some embodiments, the disease includes a malignancy. In some embodiments, the disease includes a tumor. In some embodiments, the tumor cannot be removed surgically. In some embodiments, the tumor is a solid tumor. In some embodiments, the cancer includes pancreatic cancer, head and neck cancer, breast cancer, cervical cancer, prostate cancer, retinal cancer, thyroid cancers, lymphomas, meningiomas, brain tumors, or neuroendocrine tumors.

In a fifth aspect, the disclosure features a method of causing cell death by contacting a cell with the radiopharmaceutical of the first aspect or the pharmaceutical composition of the second aspect.

In some embodiments, the cell is in a subject. In some embodiments, the cell is a cancer cell. In some embodiments, the cancer includes pancreatic cancer, head and neck cancer, breast cancer, cervical cancer, prostate cancer, retinal cancer, thyroid cancers, lymphomas, meningiomas, brain tumors, or neuroendocrine tumors.

In some embodiments of the fourth aspect or the fifth aspect, the radiopharmaceutical or pharmaceutical composition is administered into diseased tissue. In some embodiments, the radiopharmaceutical or pharmaceutical composition has an activity of at least 0.125 kBq per mL of the diseased tissue. In some embodiments, the diseased tissue is a tumor. In some embodiments, the diseased tissue is a solid tumor.

Definitions

To facilitate an understanding of this disclosure, a number of terms are defined below. Terms defined herein have meanings as commonly understood by a person of ordinary skill in the areas relevant to the disclosure. Terms such as "a," "an," and "the" are not intended to refer to only a singular entity but include the general class of which a specific example can be used for illustration. The terminology herein is used to describe specific embodiments of the disclosure, but their usage does not limit the disclosure, except as outlined in the claims.

As used herein, the term "about" refers to a value that is within 10% above or below the value being described.

By "administering" or "administration" is meant the deployment of a therapeutic composition to a target site for treatment. Administration may refer to, e.g., parenteral administration. As used herein, "parenteral administration" refers to administration of a composition characterized by physical breaching of the tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. Parenteral administration is contemplated to include intravascular administration, subcutaneous administration, intraperitoneal administration, intramuscular administration, and intrasternal administration. In some embodiments, administration is directly into diseased tissue (e.g., tumor tissue). In some embodiments, administration is proximal to diseased tissue (e.g., within 10 mm, within 5 mm, within 4 mm, within 3 mm, within 2 mm, or within 1 mm).

As used herein, the term "Auger emitter" refers to an atom, ion, or molecule which emits a low energy electron, called an "Auger electron" in response to a vacancy in an inner shell atomic orbital. The vacancy can be created either by interaction with a high energy source (e.g., an X-ray photon or an electron beam) or by proton capture.

As used herein, "α-emitting radionuclide," or alternatively "alpha-radionuclide," "alpha emitter," or "α-emitter," refers to an atom, ion, or molecule which radioactively decays via the emission of an alpha particle (also referred to as an α particle, an $\alpha^{2+}$ particle, a helium-4 nucleus, $He^{2+}$, or $_2^4He$).

As used herein, "β-emitting radionuclide," or alternatively, "β-radionuclide," "beta emitter," or "β-emitter," refers to an atom, ion, or molecule which radioactively decays via the conversion of a proton to a neutron coupled with the emission of a $β^-$ particle (i.e., an electron) or the conversion of a neutron to a proton coupled with the emission of a $β^+$ particle (i.e., a positron).

By "biodegradable," as used herein, is meant any material which the body of a subject is capable of removing by breaking down (e.g., metabolic degradation, absorption, phagocytosis, or enzymatic digestion) the material and/or by filtering the material out of the body (e.g., via the kidney or liver), and excreting it (e.g., via the bowel). Biodegradable materials may also be considered non-toxic.

By "cell-penetrating ligand" is meant any material which facilitates movement of a material (such as the ligand and a component(s) bound or conjugated to the ligand) across a cell membrane. The cell-penetrating ligand can be one that confers energy-independent (i.e., non-endocytolytic) translocation properties associated with the transport of a radiopharmaceutical of the present disclosure across the plasma and/or nuclear membranes of a cell. A cell-penetrating ligand may be included to slow washout of a radiopharmaceutical composition from the vasculature of a subject. Cell-penetrating ligands include "cell-penetrating polypeptides," short (e.g., from about 5 amino acids to about 50 amino acids) peptides which stimulate endocytosis of cells, facilitating the uptake of the cell-penetrating ligand and anything to which it may be conjugated.

By "chelation," as used herein, refers to a bond between a metal atom or ion and an organic moiety. In some embodiments, more than one bond may exist between the metal atom or ion and an organic moiety. In some embodiments, the organic moiety is a carboxylate, phosphate, amine, thiol, or cyano.

By "treating" or "treatment" is meant the medical management of a subject with the intent that an amelioration, repair, or prevention of a further injury, disease, pathological condition, or disorder will result. Treatment or treating include: active treatment, that is, treatment directed specifically toward improvement of the injury or disease, pathological condition, or disorder, and also includes causal treatment, that is, treatment directed toward removal of the cause of the injury or disease, pathological condition, or disorder. In addition, this term includes palliative treatment, that is, treatment designed for the relief of symptoms rather than the curing of the injury or disease, pathological condition, or disorder; preventive treatment, that is, treatment directed to prevention of the injury or disease, pathological condition, or disorder; and supportive treatment, that is, treatment employed to supplement another specific therapy directed toward the improvement of the injury or disease, pathological condition, or disorder. Treatment or treating includes, e.g., reduction in the size of a tumor, decreased metastasis of tumoral tissue, or improved health of the tissue surrounding a tumor.

As used herein, "radionuclide," or alternatively "radioactive nuclide" or "radioactive nucleus," refer to any atom, ion, or molecule which undergoes radioactive decay. In some embodiments, radioactive decay is accompanied by the release of ionizing radiation (i.e., radiation sufficient to remove an electron from an atom, ion, or molecule). Exemplary radionuclides include α-emitters (e.g., astatine-211, actinium-225, bismuth-213, bismuth-212, lead-212, thorium-226, terbium-149, thorium-227, radium-223, or radium-224) and β-emitters (e.g., yttrium-90, iodine-131, holmium-166, lutetium-177, lead-210, bismuth-214, thallium-206, strontium-90, technetium-99, cesium-137, carbon-14, sulfur-35, or hydrogen-3).

As used herein, any values provided in a range of values include both the upper and lower bounds, and any values contained within the upper and lower bounds.

BRIEF DESCRIPTION OF DRAWINGS

FIGS. 1A-1B show the structure of nanoparticles of the disclosure. FIG. 1A shows a nanoparticle encapsulating an imaging agent (e.g., iohexol; represented by a star) and a radionuclide (RN). The radionuclide is complexed by the chelating agent 1,4,7,10-tetraazacyclododecane-1,4,7,10-tetraacetate (DOTA). The chelated radionuclide is represented by a lightning bolt. FIG. 1B shows the modification of a nanoparticle of FIG. 1A with a cell-penetrating ligand, such as TAT, which is represented by a spiral.

FIGS. 2A-2C show nanoparticles of the disclosure that include a sub-nanoparticle. FIG. 2A shows the structure of a single sub-nanoparticle including an imaging agent (e.g., iohexol; represented by a star) and a chelated radionuclide (e.g., a DOTA chelated radionuclide; represented by a lightning bolt). FIG. 2B shows a schematic illustrating the encapsulation of the sub-nanoparticle of FIG. 2A within a nanoparticle. Leakage of the imaging agent or the radionuclide from the sub-nanoparticle is reduced by encapsulating the sub-nanoparticle within the nanoparticle. The sub-nanoparticle and the nanoparticle may be made of the same polymeric material (e.g., PLGA) or different polymeric materials. Alternatively, the sub-nanoparticle may include or be made from a metallic matrix (e.g., $Fe_2O_3$) and the nanoparticle may include or be made from a polymer matrix. The diameter of the nanoparticle may be approximately 20 times the diameter of the sub nanoparticle. FIG. 2C shows modification of the nanoparticle of FIG. 2B with a cell-penetrating ligand, such as TAT, which is represented by a spiral.

DETAILED DESCRIPTION

The present disclosure features radiopharmaceutical compositions including a radionuclide and an imaging agent incorporated into a nanoparticle and methods of their use. The radionuclide and/or imaging agent may be encapsulated inside the nanoparticle. The radiopharmaceutical may further include a cell-penetrating ligand and/or a complexing moiety conjugated to the exterior surface of the nanoparticle. Optionally, the radiopharmaceutical compositions may also include a sub-nanoparticle encapsulated inside the nanoparticle. The sub-nanoparticle may also include a radionuclide and/or imaging agent that is encapsulated inside or embedded in a matrix of the sub-nanoparticle. The radiopharmaceutical compositions can be formulated for direct administration to the tissue or organ (e.g., a disease organ or tissue) of a subject with minimal or no washout of the radiopharmaceutical to non-target sites within the subject. The radiopharmaceutical compositions of the present disclosure allow for efficient treatment of diseased tissue (e.g., cancer) that is proximal to the site of administration with minimal to no damage to surrounding tissue.

Nanoparticles

The present disclosure features radionuclides encapsulated or embedded in a nanoparticle. Current radiopharmaceutical technologies suffer from a lack of specificity in targeting diseased tissue. Most radiopharmaceuticals known in the art are formulated for intravenous administration, and therefore a large portion of the injected dose will be taken up by other organs such as the kidneys and the liver, resulting in large doses of radiation at these non-target sites (i.e., sites within healthy tissue). The present disclosure avoids these limitations by connecting the radionuclides to nanoparticles (e.g., encapsulating the radionuclide in the nanoparticle, embedding the radionuclide in the surface of the nanoparticle, or binding the radionuclide to a nanoparticle via a complexing moiety). These nanoparticles serve not only to localize the radionuclide to the site of administration, but can also be functionalized to include, e.g., an imaging agent and/or a cell-penetrating ligand, which may aid in treatment efficacy and/or pre- or post-treatment diagnostics.

The nanoparticles of the present disclosure are composed of a matrix defining the structure (e.g., size or shape) and material the nanoparticle includes or is formed from. The nanoparticle matrix may form the core of the nanoparticle (e.g., a core made of a material, e.g., a polymer core or a metal-containing core), into which components of the radiopharmaceutical (e.g., the complexing moiety, the radionuclide, the imaging agent, or the cell-penetrating ligand), may be encapsulated within, embedded in, or bound to.

The nanoparticle of the present disclosure may be substantially spherical, elliptical, rod-shaped, cylindrical, or prismatic. The nanoparticle may be irregularly shaped. The diameter of the nanoparticle may be at most about 1000 nm (e.g., at most 900 nm, at most 800 nm, at most 700 nm, at most 600 nm, at most 500 nm, at most 400 nm, at most 300 nm, at most 200 nm, at most 150 nm, at most 100 nm, at most 75 nm, at most 50 nm, at most 40 nm, or at most 30 nm). The diameter of the nanoparticle may be from about 1 nm to about 900 nm (e.g., from about 2 nm to about 850 nm, from about 3 nm to about 800 nm, from about 4 nm to about 750 nm, from about 5 nm to about 700 nm, from about 6 nm to about 650 nm, from about 7 nm to about 550 nm, from about 8 nm to about 500 nm, from about 9 nm to about 450 nm, from about 10 nm to about 400 nm, from about 15 nm to about 350 nm, from about 20 nm to about 300 nm, from about 25 nm to about 250 nm, or from about 30 nm to about 200 nm). The nanoparticle may be sized to preclude venous absorption of the nanoparticle.

The nanoparticle matrix may be a polymer matrix (e.g., a nanoparticle with a polymer core). Polymer matrices, as used herein, refers to any nanoparticle matrix which includes at least one organic polymer. The organic polymer may be non-toxic, biocompatible, and/or hydrophilic. The polymer matrix may include or be formed from polyglycolide (PGA), polylactide (PLA), poly(lactide-co-glycolide) (PLGA), polycaprolactone (PCL), poly(alkenedicarboxylate) s (e.g., poly(butylene succinate) (PBS), poly(ethylene succinate) (PES), poly(butylene succinate-co-adipate) (PBSA), or poly (p-dioxanone) (PPDO)), polycarbonates (e.g., poly(trimethylene carbonate) (PTMC), poly(propylene carbonate), or poly [oligo (tetramethylene succinate)-co(tetramethylene carbonate)]), aromatic copolyesters (e.g., poly(butylene adipate-co-terephtalate) (PBAT), poly(ethylene terephtalate), BIOMAX®, ECOFLEX®, ORIGO-BI®, poly(β-hydroxyalcanoate), xanthan, curdlan, pullulan, poly(hydroxybutyrate) (PHB), or poly(hydroxybutyrate-co-hydroxyvalerate) (PHBV)), polyamides and polypeptides (e.g., aliphatic poly(ester-amide) s, copolymers of 1,2-ethanediol, adipic acid and amino acids (including glycine and phenylalanine), CAMEO®, or BAK 1095®), polyanhydrides (e.g., poly (sebacic anhydride)), polysaccharides (e.g., chitin, chitosan, starch, poly-α-1,4-D-glucopyranoside (amylose), poly-α-1, 4-Dglucopyranoside-α-1,6-D-glucopyranoside (amylopectine), cellulose, cellulose esters, cellulose acetate, microcrystalline cellulose, carboxymethylcellulose, lignocellulose, alginic acid, sodium alginate, calcium alginate, hyaluronic acid, or chondroitin sulphate), proteins (e.g., gelatin, gelatine grafts, soy protein, wheat gluten, collagen, elastin, albumin, or fibrin), oils, fatty acids, methyl methacrylate poly(ethyl acrylate), polymer blends (e.g., starch blends (e.g., starch-poly(ethylene-co-vinyl alcohol) (EVOH), starch-polyvinyl alcohol, starch-PLA, starch—PCL, starch—PBS, or starch—PHB), blends of PHBV and PPC, blends of poly(aspartic acid-co-lactide) (PAL) and PLLA, blends of PAL and PBS, or blends of PAL and PCL), poly(propylene fumarate) (PPF), poly(E-caprolactone-fumarate), or any copolymer, block-copolymer, dendrimer, or mixture thereof. Additional polymer materials are known in the art (see, e.g., U.S. Pat. No. 10,058,633; the biodegradable matrices of which are incorporated herein by reference).

The polymer nanoparticle may include hyaluronic acid (HA), polyethylene glycol diacrylate (PEGDA), polyglycolic acid (PGA), polylactic acid (PLA), poly(lactic-co-glycolic acid) (PLGA), polysaccharide, polycaprolactone (PCL), Collagen, Gelatin, poly(methyl methacrylate) (PMMA), polystyrene, carboxymethyl chitosan (CCN), carboxymethyl cellulose (CMC), phospholipids, or a combination thereof.

The nanoparticle may include a sub-nanoparticle. A sub-nanoparticle is a defined nanoparticulate structure encapsulated within the nanoparticle matrix. The sub-nanoparticle may be substantially spherical, elliptical, rod-shaped, cylindrical, or prismatic. The sub-nanoparticle may be irregularly shaped.

The diameter of the sub-nanoparticle may be from about 1 nm to about 10 nm (e.g., from about 2 nm to about 9 nm, from about 3 nm to about 8 nm, from about 4 nm to about 7 nm, from about 5 nm to about 6 nm, about 1 nm, about 2 nm, about 3 nm, about 4 nm, about 5 nm, about 6 nm, about 7 nm, about 8 nm, about 9 nm, or about 10 nm).

The sub-nanoparticle may include or be formed from a polymeric matrix. The sub-nanoparticle polymer matrix may include or be formed from polyglycolide (PGA), polylactide (PLA), poly(lactide-co-glycolide) (PLGA), polycaprolactone (PCL), poly(alkenedicarboxylate) s (e.g., poly(butylene succinate) (PBS), poly(ethylene succinate) (PES), poly(butylene succinate-co-adipate) (PBSA), or poly(p-dioxanone) (PPDO)), polycarbonates (e.g., poly(trimethylene carbonate) (PTMC), poly(propylene carbonate), or poly[oligo (tetramethylene succinate)-co(tetramethylene carbonate)]), aromatic copolyesters (e.g., poly(butylene adipate-co-terephtalate) (PBAT), poly(ethylene terephtalate), BIOMAX®, ECOFLEX®, ORIGO-BI®, poly(β-hydroxyalcanoate), xanthan, curdlan, pullulan, poly(hydroxybutyrate) (PHB), or poly(hydroxybutyrate-co-hydroxyvalerate) (PHBV)), polyamides and polypeptides (e.g., aliphatic poly(ester-amide) s, copolymers of 1,2-ethanediol, adipic acid and amino acids (including glycine and phenylalanine), CAMEO®, or BAK 1095®), polyanhydrides (e.g., poly(sebacic anhydride)), polysaccharides e.g., (chitin, chitosan, starch, poly-α-1,4-D-glucopyranoside (amylose), poly-α-1, 4-Dglucopyranoside-α-1,6-D-glucopyranoside (amylopectine), cellulose, cellulose esters, cellulose acetate, microcrystalline cellulose, carboxymethylcellulose, lignocellulose, alginic acid, sodium alginate, calcium alginate, hyaluronic acid, or chondroitin sulphate), proteins (e.g., gelatin, gelatine grafts, soy protein, wheat gluten, collagen, elastin, albumin, or fibrin), oils, fatty acids, methyl methacrylate poly(ethyl acrylate), polymer blends (e.g., starch blends (e.g., starch-poly(ethylene-co-vinyl alcohol) (EVOH), starch-polyvinyl alcohol, starch-PLA, starch—PCL, starch—PBS, or starch—PHB), blends of PHBV and PPC, blends of poly(aspartic acid-co-lactide) (PAL) and PLLA, blends of PAL and PBS, or blends of PAL and PCL), poly(propylene fumarate) (PPF), poly(E-caprolactone-fumarate), or any copolymer, block-copolymer, dendrimer, or mixture thereof. Additional sub-nanoparticle materials are known in the art (see, e.g., U.S. Pat. No. 10,058,633; the matrices of which are incorporated herein by reference).

The sub-nanoparticle matrix may include hyaluronic acid (HA), polyethylene glycol diacrylate (PEGDA), polyglycolic acid (PGA), polylactic acid (PLA), poly(lactic-co-glycolic acid) (PLGA), polysaccharide, polycaprolactone (PCL), Collagen, Gelatin, poly(methyl methacrylate) (PMMA), polystyrene, carboxymethyl chitosan (CCN), carboxymethyl cellulose (CMC), phospholipids, or a combination thereof.

Alternatively, the sub-nanoparticle matrix may include a metal matrix. Exemplary metal matrices include iron, gold, platinum, tantalum, an oxide thereof (e.g., magnetite ($Fe_3O_4$), maghemite ($\gamma\text{-}Fe_2O_3$), or hematite ($\alpha\text{-}Fe_2O_3$)), or an alloy thereof.

The radionuclide may be localized within the sub-nanoparticle. For example, the sub-nanoparticle may include a radionuclide encapsulated in the sub-nanoparticle matrix (i.e., encapsulated on all sides by the sub-nanoparticle matrix). The sub-nanoparticle may then be further encapsulated in the nanoparticle matrix, thereby localizing the radionuclide within the nanoparticle. This localization serves to prevent disassociation or leakage of radionuclides from the nanoparticle, as no radionuclides are located on the exterior surface of the nanoparticle, and therefore no radionuclides can dissociate therefrom.

The nanoparticle matrix or sub-nanoparticle matrix may be modified (e.g., functionalized) to promote the formation of a covalent bond between the nanoparticle and a ligand (e.g., a biomolecule, e.g., a cell-penetrating ligand or the complexing moiety). For example, the nanoparticle matrix may include or be functionalized to include a reactive functional group (e.g., a silane, a siloxane, an amine, an amide, a hydroxide, a carboxylate, a sulfamide, etc.). The nanoparticle matrix may be modified prior to the formation of the nanoparticle (e.g., the polymer may be or include a biodegradable polymer, e.g., a functionalized derivative of a biodegradable polymer described herein) or functionalized after the formation of the nanoparticle (e.g., subjecting a nanoparticle, e.g., a nanoparticle formed by a method described herein, to a further chemical reaction to functionalize the nanoparticle matrix).

Complexing Moiety

Any chemical component conjugated to the exterior surface of the nanoparticle (e.g., the radionuclide or cell-penetrating ligand) may be conjugated to the exterior surface of the nanoparticle via a complexing moiety. A complexing moiety, as defined herein, refers to any chemical capable of simultaneously binding to the surface of the nanoparticle (e.g., through a covalent bond, chelation, or electrostatic interaction) and to the chemical component (e.g., through a covalent bond, chelation, or electrostatic interaction). The complexing moiety may be capable of binding to a reactive substrate (e.g., an ion or a radionuclide; referred to as a "reactive" complexing moiety).

The complexing moiety may include an organic linker with a proximal end and a distal end. The proximal end of the complexing moiety includes an organic moiety configured to conjugate the complexing moiety to the nanoparticle. The distal end of the complexing moiety includes an organic moiety configured to conjugate the complexing moiety to the chemical component (e.g., to a radionuclide (e.g., a separate radionuclide from the radionuclide enclosed within the nanoparticle), or the cell-penetrating ligand). Examples of organic moieties to be included at the proximal end or the distal end of the complexing moiety include a carboxylate, phosphate, amine, thiol, or cyano groups. Alternatively, an organic moiety may include a chelating ligand (e.g., diethylenetriaminepentaacetate (DTPA), 1,4,7,10-tetraazacyclododecane-1,4,7,10-tetraacetate (DOTA), ethylenediamine tetraacetate (EDTA), cis-1,3,5-cyclohexantriamine (CHTA), triethylene glycol diamine tetraacetate (EGTA), 1,4,8,11-tetraazacyclotetradecane-1,4,8,11-tetraacetate (TETA), 1,4,7,10-tetraazacyclododecane-1,4,7-triacetate (DO3A), 1,4,7-triazacyclononane-1,4,7-triacetate (NOTA), 1,4,7,10,13,16-hexaazacyclooctadecane-1,4,7,10,13,16-hexaacetate (HEHA), N,N'-[(6-carboxy-2-pyridyl(methyl)]-4,13-diaza-18-crown-6 (MACROPA), 1,4,7,10-tetraazacyclododecane-1,7-diacetate (DO2A), 1,4,7,10-tetraazacyclododecane-1,4,7,10-tetraacetic amide (DOTAM), a reactive derivative thereof, or a combination thereof).

Radionuclides

Radiopharmaceuticals of the present disclosure include a radionuclide (e.g., embedded in the surface of the nanoparticle or encapsulated within the nanoparticle. Radionuclides are atoms, ions, or molecules including said atoms or ions, which undergo radioactive decay, converting the nucleus of the radionuclide atom or ion to a second atom or ion. The second atom or ion is referred to as the "daughter nucleus." A radionuclide may be characterized by its half-life ($t_{1/2}$), the time it takes for half the mass of a radioactive composition to undergo radioactive decay. Due to the high energy associated with this nuclear conversion, radionuclides are capable of releasing incredibly high doses of energy into the surrounding environment. The radioactivity of a radionuclide is often measured in terms of "activity," or the number of nuclear decay events per second, measured in units of becquerel (Bq, 1 Bq=1 $s^{-1}$, corresponding to the number of decay events of the radionuclide per second). The intensity of this energy absorbed by a proximal material is often measured in "radiation absorbed dose," provided in units of "rads" or "grays" (Gy), with 1 rad being equivalent to 0.01 J of emitted energy from radioactive decay per kg of the proximal material absorbing the energy, and 1 Gy being equivalent to 100 rads. A radionuclide whose radiation intensity is sufficient to elicit a therapeutic effect may be referred to as a "therapeutic radionuclide" herein.

A radionuclide of the present disclosure may further include a chelating agent bound to the radionuclide. The presence of the chelating agent may increase the stability of the radionuclide (and therefore the nanoparticle) to chemical degradation. Exemplary chelating agents include, e.g., diethylenetriaminepentaacetate (DTPA), 1,4,7,10-tetraazacyclododecane-1,4,7,10-tetraacetate (DOTA), ethylenediamine tetraacetate (EDTA), cis-1,3,5-cyclohexantriamine (CHTA), triethylene glycol diamine tetraacetate (EGTA), 1,4,8,11-tetraazacyclotetradecane-1,4,8,11-tetraacetate (TETA), 1,4,7,10-tetraazacyclododecane-1,4,7-triacetate (DO3A), 1,4,7-triazacyclononane-1,4,7-triacetate (NOTA), 1,4,7,10,13,16-hexaazacyclooctadecane-1,4,7,10,13,16-hexaacetate (HEHA), N,N'-[(6-carboxy-2-pyridyl(methyl)]-4,13-diaza-18-crown-6 (MACROPA), 1,4,7,10-tetraazacyclododecane-1,7-diacetate (DO2A), 1,4,7,10-tetraazacyclododecane-1,4,7,10-tetraacetic amide (DOTAM), a reactive derivative thereof, or a combination thereof.

Several pathways of radioactive decay are known, such as α decay and β decay (including $β^-$ and $β^+$ decay). Each decay pathway is named for the type of particle produced during decay (e.g., an α particle, a $β^-$ particle, or a $β^+$ particle). The radionuclide may undergo α decay by the emission of an α particle, β decay by the emission of a β particle, or a combination thereof.

The nucleus produced by radioactive decay (i.e., the "daughter nucleus") may also be a radionuclide, which may undergo α decay, β decay, or a combination thereof. This may increase the ablation energy density of the radiopharmaceutical.

Radioactive decay, particularly β-decay, may result in a daughter nucleus with an electron hole in an inner-shell atomic orbital (e.g., as a result of electron capture). In such cases, the resulting species may undergo a further process known as "Auger emission" wherein an outer shell electron transitions to the inner shell to fill the vacancy, simultaneously releasing a low energy electron (a "Auger electron"). Auger electrons are typically emitted at energies suitable to cause DNA damage. Accordingly, radionuclides whose daughter particles emit Auger electrons are suitable for the compositions of the present disclosure.

A radionuclide may be characterized by its half-life. The radionuclide may have a $t_{1/2}$ of 1 hour to up to 30 days (e.g., 1, 2, 3, 4, 5, 6, 7, 8, 9, 10, 11, 12, 13, 14, 15, 16, 17, 18, 19, 20, 21, 22, 23, or 24 hours or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days). Preferably, radionuclides of the present disclosure have a $t_{1/2}$ of 6 hours to 21 days. A radionuclide may be considered to be providing radiation to the environment proximal to it for at most 10 half-lives (i.e., the time it takes for about 99.9% of a radionuclide to undergo radioactive decay). The majority of radiation is considered to have been delivered by a radionuclide within the first 4 half-lives (i.e., the time it takes for about 94% of the radionuclide to undergo radioactive decay).

The radiopharmaceutical may be formulated such that the specific activity of the radiopharmaceutical is sufficient to kill tumor cells proximal to the nanoparticle. For example, the specific activity of each radiopharmaceutical is from about 0.01 µBq per radiopharmaceutical to about 10 µBq per radiopharmaceutical (e.g., from about 0.02 µBq per radiopharmaceutical to about 8 µBq per radiopharmaceutical, from about 0.03 µBq per radiopharmaceutical to about 6 µBq per radiopharmaceutical, from about 0.4 µBq per radiopharmaceutical to about 4 µBq per radiopharmaceutical, or from about 0.2 µBq per radiopharmaceutical to about 2 µBq per radiopharmaceutical).

α-Emitting Radionuclide

The radionuclide may be an α-emitting radionuclide, alternatively referred to as an "α-radionuclide," an "alpha emitter," or an "α-emitter." Alpha-emitting radionuclides are atoms, ions, or molecules which radioactively decay via the emission of an α particle (also referred to as an α particle, an $α^{2+}$ particle, a helium-4 nucleus, $He^{2+}$, or $_2^4He$). A representative radionuclide A with P protons, N neutrons, and an atomic weight of P+N may radioactively decay to nuclide B with P−2 protons, N−2 neutrons, and an atomic weight of P+N−4 while emitting an α particle as represented by:

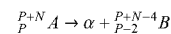

$$_P^{P+N}A \rightarrow \alpha + _{P-2}^{P+N-4}B$$

α particles may have an energy of from about 1 MeV to about 10 MeV, depending on the size of the radionuclide. For example, the emitted particle may have an energy of from about 3 MeV to about 7 MeV.

Due to their large mass (4 atomic mass units, or about $6.64 \times 10^{-27}$ kg) relative to β particles, α particles are easily absorbed by most materials, and therefore have a correspondingly small penetration depth into biological tissue (e.g., at most about 100 µm, at most about 90 µm, at most about 80 µm, at most about 70 µm, at most about 60 µm, at most about 50 µm, at most about 40 µm, at most about 30 µm, at most about 20 µm, at most about 10 µm, at most about 5 µm, or at most about 1 µm). The area of tissue irradiated by an α particle emitted from a radionuclide is referred to as "proximal to" the radionuclide herein. An α emitting radionuclide or a composition containing the same may be administered to a subject at the site of desired ablation, ablating proximal cells, resulting in cell death of the proximal cells.

α-emitting radionuclides offer distinct advantages for treatment of neoplastic tissues (e.g., malignancies). First, the very short range of α particles in soft tissue allows for selective elimination of the target cells while sparing the surrounding healthy tissue. This effect, coupled with their high energy density, imparts a high cell-killing efficacy per distance traveled through the tissue. In other words, α-emitting radionuclides are highly efficient at killing cells proximal to the site of administration (e.g., diseased tissue) while causing minimal damage to cells or tissue further away (e.g., healthy tissue).

α particles interacting with biological tissue may cause double strand breaks and cluster DNA breaks, a process that is largely independent of cell cycle and oxygenation status. Consequently, α radiation can induce apoptosis in cells that are resistant to other forms of ionizing radiation or chemotherapeutic drugs. This makes α particles particularly amenable to treatment of cancers resistant to chemotherapeutic drugs.

Exemplary α-emitters include astatine-211, actinium-225, bismuth-213, bismuth-212, lead-212, thorium-226, terbium-149, thorium-227, radium-223, and radium-224. Further examples are known in the art (see, e.g., Poty et al.; α-Emitters for Radiotherapy: From Basic Radiochemistry to Clinical Studies—Part 1, *J. Nuc. Med.* 2018, 59:878-884; and Trujilo-Nolasco et al.; Nanoradiopharmaceuticals Based on Alpha Emitters: Recent Developments for Medical Application, *Pharmaceutics*, 2021, 13 (8): 1123; the α-emitters of which are incorporated herein by reference).

β-Emitting Radionuclide

The radionuclide may be a β-emitting radionuclide, alternatively referred to as a "β-radionuclide," a "beta emitter," or a "β-emitter." β-emitting radionuclides are atoms, ions, or molecules which radioactively decay via the conversion of a proton to a neutron coupled with the emission of a β⁻ particle (i.e., an electron) or the conversion of a neutron to a proton coupled with the emission of a β⁺ particle (i.e., a positron). A representative radionuclide A with P protons, N neutrons, and an atomic weight of P+N may radioactively decay via β-decay to a nuclide B with P−1 protons, N+1 neutrons, and an atomic weight of P+N while emitting a β⁻ particle as represented by:

$$^{P+N}_{P}A \rightarrow \beta^- + ^{P+N}_{P-1}B$$

Alternatively, representative radionuclide A with P protons, N neutrons, and an atomic weight of P+N may radioactively decay via β⁺ decay to a nuclide B with P+1 protons, N−1 neutrons, and an atomic weight of P+N while emitting a β⁺ particle as represented by:

$$^{P+N}_{P}A \rightarrow \beta^+ + ^{P+N}_{P+1}B$$

β particles may have an energy of from about 0.01 MeV to about 1 MeV (e.g., from about 0.1 MeV to about 0.9 MeV, from about 0.2 MeV to about 0.8 MeV, from about 0.3 MeV to about 0.7 MeV, from about 0.4 MeV to about 0.6 MeV, or about 0.5 MeV).

β particles are more penetrating than α particles, due to their smaller size and lower energy range. β particles typically penetrate less than about 1 cm (e.g., about 1 cm, about 0.9 cm, about 0.8 cm, about 0.7 cm, about 0.6 cm, about 0.5 cm, about 0.4 cm, about 0.3 cm, about 0.2 cm, about 0.1 cm, or about 0.05 cm) into biological tissue. β particles are considered less damaging to biological tissue than α particles, as they are capable of traveling farther into most biological tissue without being absorbed. A radiopharmaceutical of the present disclosure may employ a β emitting radionuclides, e.g., when ablation at a large distance from the administration site (e.g., at least 100 μm from the administration site, at least 1 mm from the administration site, at least 10 mm from the administration site, or at least 100 mm from the administration site) is desired.

Examples of β-emitters include yttrium-90, iodine-131, holmium-166, lutetium-177, lead-210, bismuth-214, thallium-206, strontium-90, technetium-99, cesium-137, carbon-14, sulfur-35, and hydrogen-3.

Auger Emitters

The radionuclide or its daughter particle may be an Auger emitter. Auger emitters are atoms, ions, or molecules which emit a low energy electron—referred to as an Auger electron—in response to an electron hole in an inner shell atomic orbital. The hole may result from excitation with an external energy source (e.g., an X-ray photon or an electron beam). Alternatively, the hole may be created from an electron capture of an electron inn inner shell orbital. An outer shell electron transitions to the inner shell to fill the hole, releasing energy. The energy release may then be transferred to a second outer shell electron (the Auger electron), which is then ionized from the atom with an energy equal to the energy difference between the vacancy filling transition and the ionization energy of the Auger electron.

Auger emitters are promising radionuclides for cancer treatment, as Auger electrons have a fairly short path length (on the order of micrometers) in biological tissues, with a high linear energy transfer. Further, many Auger emitters emit Auger electrons of a fairly low energy (e.g., less than 100 keV, less than 75 keV, less than 50 keV, less than 25 keV, less than 20 keV, less than 15 keV, less than 10 keV, or less than 5 keV) Auger electrons are therefore efficient in causing local DNA damage (e.g., double strand breaks). Further, Auger electrons may result in the formation of free radicals (e.g., reactive hydroxyl radicals) which may cause further DNA damage. A radiopharmaceutical of the present disclosure may employ an Auger emitter, e.g., when ablation at an intermediate distance from the administration site (e.g., from about 10 nm to about 100), or a low dose of radiation energy is desired.

The radionuclide of the present disclosure may be a radionuclide which produces Auger electrons during radioactive decay, e.g., during a β-decay process. The Auger emitter is the daughter nuclei of such a radionuclide. The daughter nuclei may include an inner shell hole and spontaneously undergo Auger emission. Exemplary radionuclides which produce Auger electrons during decay include indium-111, gallium-67, technetium-99m, platinum-195m, iodine-125, and iodine-123.

Imaging Agents

The radiopharmaceutical of the present disclosure can also include an imaging agent encapsulated within the nanoparticle. Imaging agents are compounds which allow for the visualization of a material during an imaging procedure. Radionuclide compositions known in the art commonly suffer because they lack any means by which a practitioner may discern the location of the radiopharmaceutical in the body of a subject, limiting the practitioner's ability to monitor treatment progression and adjust, e.g., treatment dose and duration. By encapsulating an imaging agent within the nanoparticle, along with the radionuclide, the imaging agent and the radionuclide are co-localized. This allows for the location of the radionuclide to be monitored both during and after administration of the radiopharmaceutical.

Imaging agents serve to change the relative signal differences observed in an imaging procedure, either by increasing, decreasing, or otherwise modulating the signal. For example, an X-ray imaging agent may have a larger X-ray attenuation than the biological tissue to be imaged, causing a larger amount of absorbed X-rays by the radiopharmaceutical. The imaging agents of the present disclosure may then be visible during an imaging procedure, allowing a practitioner to monitor and adjust a treatment procedure as required.

Imaging agents featured in the present disclosure are encapsulated within a nanoparticle, thereby localizing the imaging agent to the site of treatment and improving the imaging of the nanoparticle composition (e.g., by at least 10 Hounsfield units) compared to the surrounding tissue. The nanoparticle may include a sub-nanoparticle and both may include an imaging agent. The imaging agent embedded in or encapsulated within the nanoparticle and the sub-nanoparticle may be different. This would facilitate multiple different methods for imaging the tissue of a subject, thereby improving the quantity and quality of data obtained during procedures using the radiopharmaceutical.

Imaging agents may be chosen for use with a particular type of imaging modality. For example, the imaging agent may be galactose, or lipidated sulfur perfluorobutane for use in ultrasonic imaging; Iodixanol, Iohexol, Iohexol related compound B, or diatrizoic acid for use in X-ray imaging (e.g., fluoroscopy and computed tomography); Feraheme, gadolinium, holmium, europium, thulium copper-64, technetium-99m, and indium-111 for use in magnetic resonance imaging (MRI); iodine-123, technetium-99m, thallium-201, and fluorine-18 for single photon emission computed tomography; or fluorine-18 for positron emission tomography. Any combination of imaging modalities and/or imaging agents (e.g., any combination of imaging modalities and imaging agents described herein) may also be used. The nanoparticles of the present disclosure may include components or features that allow them to be visualized using X-ray based imaging modalities and MRI based imaging modalities.

Further examples of imaging agents are known in the art (see, e.g., International Patent Publication Nos.: WO 2011/097649; WO 2011/143360; WO 2009/092062; WO 2012/100206; WO 2014/152389; WO 1984/002838; WO 2012/007456; WO 1994/014478; WO 2021/044153; WO 2015/040128; WO 2005/070400; WO 2019/083990; WO 2015/196208; and WO 2015/058151; U.S. Pat. Nos. 4,774,958; 6,818,199; 9,433,392; 7,534,418; 9,597,419; 9,694,742; and 9,738,596; and US Patent Publication No. 2010/0032575; the imaging agents and contrast agents of which are incorporated herein by reference).

Cell-Penetrating Ligands

The radiopharmaceuticals of the present disclosure may also include a cell-penetrating ligand, which can be conjugated (e.g., chelated) to the exterior surface of the nanoparticle of the radiopharmaceutical. Cell-penetrating ligands, alternatively known as cell-penetrating peptides, are a class of peptides which facilitate the transportation of materials across a cell membrane. Critically, cell-penetrating ligands are capable of doing so with minimal toxicity or damage to the cell. Cell-penetrating ligands are commonly short (e.g., from about 5 amino acids to about 50 amino acids) peptides which stimulate endocytosis of cells, facilitating the uptake of the cell-penetrating ligand. Pharmaceutical nanoparticles often suffer in clinical application due in part to their small size allowing the particle to be washed out from interstitial space (e.g., in a tumor cell) into the vasculature (e.g., the capillaries) of the cell. This has proven particularly problematic for the treatment of tumor cells with nanoparticle compositions, as tumors are known to have a thin vascular walls which undergo a facile exchange of components with their local surroundings. The possibility of washout reduces the therapeutic effect at the intended site as well risking potential damage to unintended regions in the body of a subject. By attaching a cell-penetrating ligand to the nanoparticle of the radiopharmaceutical, the nanoparticle may be more rapidly absorbed by a tumor cell, thereby limiting damage to non-target tissue. By covalently attaching the cell-penetrating ligand to a medicament such as a radiopharmaceutical described herein, the cell-penetrating ligand promotes the effective uptake of the medicament. Therefore, radiopharmaceuticals of the disclosure that include a cell-penetrating ligand exhibit a higher cellular uptake than those without a cell-penetrating ligand.

The cell-penetrating ligand is attached to the exterior surface of the nanoparticle of the radiopharmaceutical. The cell-penetrating ligand may be directly attached to the nanoparticle via a covalent interaction with the surface of the nanoparticle. The cell-penetrating ligand may be modified (e.g., functionalized) to promote covalent binding of the cell-penetrating ligand and the exterior surface of the nanoparticle. For example, the cell-penetrating ligand may include or be functionalized to include a reactive functional group (e.g., a silane, a siloxane, an amine, a carboxylate, a sulfamide, etc.). Alternatively, the cell-penetrating ligand may be attached to the surface of the nanoparticle via the complexing moiety. For example, the cell-penetrating ligand may be covalently bound to the complexing moiety, which is in turn covalently bound to the surface of the nanoparticle.

There are three classes of cell-penetrating ligands that can be used in the radiopharmaceutical: polycationic cell-penetrating ligands (which include a high density of charged lysine or arginine residues), amphipathic cell-penetrating ligands (which include an alternating pattern of polar, charged, and non-polar amino acids), and hydrophobic cell-penetrating ligands (which include only non-polar residues).

Exemplary cell-penetrating ligands include, e.g., TAT, HSV, gH625, penetratin, VP22, and transportan.

Pharmaceutical Compositions

Radiopharmaceuticals of the present disclosure may be prepared, stored, and/or administered as a pharmaceutical composition. The pharmaceutical composition includes the radiopharmaceutical suspended, dispersed, or dissolved in a pharmaceutically acceptable carrier, e.g., water, an alcohol (e.g., ethanol) a polyol (e.g., sorbitol, xylitol, mannitol, erythritol, maltitol, lactitol, isomalt, or glycerol), a polyether (e.g., polyacetal, polyethylene glycol (PEG), polypropylene glycol (PPG), polytetramethylene glycol (PTMG), or poly (epicholorhydrin)), salcaprozate sodium, sodium caprate, or a combination thereof. The excipient may be a buffered carrier (e.g., buffered glycerol, buffered water, buffered saline, or buffered ethanol). Further examples of pharmaceutically acceptable excipients include pharmaceutically acceptable salt solutions (e.g., phosphate solutions), and solutions of organic acids including salt solutions thereof. Examples of these and other pharmaceutically acceptable carriers are described in Remington's Pharmaceutical Sciences (1991, Mack Publication Co., New Jersey); Pharmaceutical Excipients: Properties, Functionality, and Applications in Research and Industry (2017, John Wiley & Sons, Inc., New Jersey); and CRC Handbook of Food, Drug, and Cosmetic Excipients; the entirety of which is incorporated herein by reference. The pharmaceutical compositions may be prepared, packaged, or sold in the form of a sterile injectable aqueous or oily suspension or solution. A pharmaceutically acceptable excipient may further include, e.g., dispersing agents, wetting agents, or suspending agents. A radiopharmaceutical nanoparticle may be lyophilized prior to hydration or solvation with an excipient.

The pharmaceutical composition may be formulated at a concentration such that its radioactivity at the time of administration is sufficient for treatment. For example, the radiopharmaceutical may have an activity of at least 0.25 kBq per mL of the pharmaceutical composition (e.g., at least 0.5 kBq per mL, at least 0.75 kBq per mL, at least 1 kBq per mL, at least 1.5 kBq per mL, at least 2 kBq per mL, etc.).

The pharmaceutical composition may include the radiopharmaceutical at a concentration sufficient to deliver a desired therapeutic dose of radiation to the target tissue of a subject. The desired therapeutic dose may be from about 1 Gy to about 500 Gy (e.g., from about 5 Gy to about 400 Gy, from about 10 Gy to about 300 Gy, from about 15 Gy to about 200 Gy, from about 20 Gy to about 100 Gy, from about 30 Gy to about 80 Gy, or from about 40 Gy to about 60 Gy).

Kits

The disclosure also features kits including a radiopharmaceutical and/or pharmaceutical composition of the present disclosure and one or more additional components, e.g., a prepared volume of the pharmaceutically acceptable excipient, a syringe, a micro puncture set, radiation shielding, a mixer, or a package insert. The kit may include the radiopharmaceutical and/or pharmaceutical composition in bulk, as a single unit dose, or as a plurality of single unit doses. The kit may include some form or radiation shielding (e.g., a lining of aluminum or lead) which allows for safe storage of the kit. The kit may further include personal protective equipment to be worn by the patient or the physician administering the radiopharmaceutical. The kit may include a mixer (e.g., a portable mixer) which can be used to stir a dispersion of the radiopharmaceutical in the excipient to ensure dissolution. The package insert may provide instructions to the user to mix the radiopharmaceutical and the excipient using the mixer for an appropriate duration. The kit may also provide components for delivering a radiopharmaceutical and/or pharmaceutical composition of the present disclosure into the body of a subject. The equipment may provide, e.g., vascular access (e.g., a syringe or a vascular access micro puncture set and access sheath; see, e.g., U.S. Pat. No. 11,027,104, the entirety of which is incorporated by reference).

Methods of Use

A radiopharmaceutical or pharmaceutical composition thereof of the present disclosure may be administered to a subject to treat a disease, condition, or disorder. The disease, condition, or disorder may be a disease, condition, or disorder of the subject's tissue. For example, the subject's tissue may include a neoplasm (e.g., a malignancy, e.g., a solid tumor). The disease, condition, or disorder may be a cancer (e.g., pancreatic cancer, head and neck cancer, breast cancer, cervical cancer, prostate cancer, retinal cancer, thyroid cancers, lymphomas, meningiomas, brain tumors, or neuroendocrine tumors). The cancer may include a tumor which cannot be removed surgically (e.g., a tumor inseparable from a vessel wall, e.g., a vessel with an encasement, or a brain tumor). The cancer may be a cancer resistant to a chemotherapy drug.

The radiopharmaceutical of the present disclosure can be formulated for direct tumoral injection. The radiopharmaceutical may be injected directly into the tumoral tissue, thereby avoiding or reducing the likelihood of rapid delocalization and washout of the radionuclide particles. This in turn allows for more directed ablation of target tissue and/or the possibility of administering a lower dose of the radionuclide, relative to other forms of therapy using the radionuclide, which may decrease the amount of damage that occurs to non-target tissue.

Each radiopharmaceutical nanoparticle may have a specific activity of from about 0.01 µBq to about 10 µBq (e.g., from about 0.02 µBq to about 8 µBq, from about 0.03 µBq to about 6 µBq, from about 0.4 µBq to about 4 µBq, or from about 0.2 µBq to about 2 µBq). The pharmaceutical composition may have an activity of 0.25 kBq per mL of the pharmaceutical composition (e.g., at least 0.5 kBq per mL, at least 0.75 kBq per mL, at least 1 kBq per mL, at least 1.5 kBq per mL, at least 2 kBq per mL, etc.). The pharmaceutical composition may have an activity of 0.125 kBq per mL of the target tissue (e.g., at least 0.25 kBq per mL, 0.375 kBq per mL, at least 0.5 kBq per mL, at least 0.625 kBq per mL, at least 0.75 kBq per mL, at least 0.875 kBq per mL, at least 1 kBq per mL, etc.).

The radiopharmaceutical may be administered in a single dose or in multiple doses. Each dose may irradiate biological tissue proximal to the site of administration for about 10 half-lives of the radionuclide. When the radiopharmaceutical is administered in multiple doses, the doses may be separated by a treatment gap. The treatment gap may be at least 10 half-lives of the radionuclide. For example, the. A treatment gap may be modified as needed depending on the needs of the patient, as known in the art.

The radiopharmaceutical may be configured to remain in the body of a subject without excretion for a duration sufficient for the subject to receive the desired therapeutic dose. During this duration, the radiopharmaceutical may not degrade or may not substantially degrade. After the duration, the radiopharmaceutical may slowly degrade (e.g., by a biodegradation pathway), and the resulting components may then be removed from the body of a subject (e.g., via urinary excretion or biliary excretion). The duration a radiopharmaceutical may remain in the body of a subject without excretion may be controlled via selection of the nanoparticle matrix. The duration may depend on the radionuclide of the radiopharmaceutical. For example, a radiopharmaceutical including a nanoparticle with a shorter half-life may be configured to remain in the body of a subject for a shorter time than a radiopharmaceutical including a radionuclide with a longer half-life.

Administration of the radiopharmaceutical may continue for a treatment duration. During the treatment duration, the response to treatment may be measured by, e.g., an imaging procedure (e.g., compatible with the imaging agent) or a blood test. The treatment duration may be from about 1 day to about 8 weeks (e.g., 2 days, 3 days, 4 days, 5 days, 6 days, 1 week, 2 weeks, 3 weeks, 4 weeks, 5 weeks, 6 weeks, or 7 weeks). The treatment duration may last until an endpoint of treatment is reached. The endpoint of treatment may be characterized by, e.g., a reduction in tumor size.

Radiopharmaceuticals of the present disclosure may be used in combination with another cancer treatment known in the art. For example, a radiopharmaceutical of the present disclosure may be administered in combination with a chemotherapeutic drug known in the art (e.g., lenalidomide, nivolumab, ibrutinib, pembrolizumab, palbociclib, atezolizumab, daratumumab, pertuzumab, enzalutamide, bevacizumab, trastuzumab, 21binutuzumab, ruxolitinib, venetoclax, or rituximab). Alternatively or additionally, a radiopharmaceutical of the present disclosure may be administered in combination with an immunotherapy known in the art (e.g., checkpoint inhibitors, chimeric antigen receptor T-cell therapy, cytokines, immunomodulators, cancer vaccines, monoclonal antibodies, or oncolytic viruses).

Method of Making

A radiopharmaceutical of the present disclosure may be synthesized using any means known in the art which can synthesize a nanoparticle and then either during synthesis or post synthetically incorporate one or more additional materials (e.g., the complexing moiety, the imaging agent, or the cell-penetrating ligand), thereby dispersing, embedding, or binding the additional material to the nanoparticle matrix (e.g., to the nanoparticle core). Exemplary methods include those disclosed in, e.g., International Patent Publication No.: WO 2010/015824; WO 2010/052455; WO 2005/044224; and WO 2009/073193; U.S. Pat. No. 8,207,290; and Plucinski et al., *Polysaccharide Nanoparticles: From Fabrication to Applications, J. Mater. Chem. B*, 2021, 9, 7030; the methods of synthesis of which are incorporated herein by reference. The radiopharmaceutical may be formed via a microfluidics process (e.g., by contacting a liquid phase including the biodegradable polymer with an antiphase at a prescribed rate to form a nanoparticle of desired size. Either the phase or the antiphase may include an additional component of the radiopharmaceutical (e.g., the radiopharmaceutical, the imaging agent, the complexing moiety). The method may allow for nanoparticles of a suitable size (e.g., a diameter of at most about 1000 nm (e.g., at most 900 nm, at most 800 nm, at most 700 nm, at most 600 nm, at most 500 nm, at most 400 nm, at most 300 nm, at most 200 nm, at most 150 nm, at most 100 nm, at most 75 nm, at most 50 nm, at most 40 nm, or at most 30 nm); or the diameter of the nanoparticle may be from about 1 nm to about 900 nm (e.g., from about 2 nm to about 800 nm, from about 3 nm to about 750 nm, from about 4 nm to about 700 nm, from about 5 nm to about 650 nm, from about 10 nm to about 550 nm, from about 15 nm to about 500 nm, from about 20 nm to about 450 nm, from about 25 nm to about 400 nm, from about 30 nm to about 350 nm, from about 35 nm to about 300 nm, from about 40 nm to about 250 nm, or from about 50 nm to about 200 nm)) to be formed. The method may allow for an encapsulation efficiency (e.g., the amount radionuclide in a reaction mixture incorporated into the nanoparticle) of as high as 99%, with resulting particle polydispersity of less than 1% and a uniform morphology.

A nanoparticle encapsulating a sub-nanoparticle(s) may be formed by first producing a sub-nanoparticle, e.g., using a method described above for producing a nanoparticle, with a diameter of from about 1 nm to about 10 nm (e.g., from about 2 nm to about 9 nm, from about 3 nm to about 8 nm, from about 4 nm to about 7 nm, from about 5 nm to about 6 nm, about 1 nm, about 2 nm, about 3 nm, about 4 nm, about 5 nm, about 6 nm, about 7 nm, about 8 nm, about 9 nm, or about 10 nm). A method of making a nanoparticle may be modified (e.g., the flow rate of a phase or antiphase in a microfluidic method may be changed) relative to a method described above to create the smaller sub-nanoparticles. As with the nanoparticle described above, an additional component of the sub-nanoparticle (e.g., the radionuclide or the imaging agent) may be encapsulated in the sub-nanoparticle with an encapsulation efficiency of as high as 99%.

After the sub-nanoparticle is formed, the sub-nanoparticle may be resuspended in a solvent. The microfluidic process may then be repeated, now including the sub-nanoparticle in the phase or antiphase. In the repeated process, the phase or the antiphase may lack any component included in the original process (e.g., a component included in the sub-nanoparticle). For example, when the sub-nanoparticle is formed including the radionuclide, the repeated process may lack the radionuclide in either the phase or the antiphase. The repeated process promotes the formation of the nanoparticle around the sub-nanoparticle, enclosing the sub-nanoparticle within the nanoparticle. This process may be used to fully encapsulate a potentially toxic or harmful component of the radiopharmaceutical, such as the radionuclide or the imaging agent, within the nanoparticle, preventing the toxic or harmful component from being located on the exterior surface of the nanoparticle. This may slow, reduce, or inhibit leakage of the toxic or harmful component from the nanoparticle after the administration to a subject. Further, enclosing a sub-nanoparticle including a radionuclide within a nanoparticle may reduce damage to non-target tissue in a subject by preventing radionuclides from diffusing away from target tissue (e.g., via the vasculature of a subject).

The as-formed nanoparticle may include a chemically reactive functional group (e.g., the biodegradable polymer may include a chemically reactive functional group). Alternatively, the as-formed nanoparticle may be post-synthetically functionalized to include a chemically reactive functional group. The reactive functional group may promote the covalent attachment of an additional ligand (e.g., a biomolecule (e.g., a cell-penetrating ligand), or a complexing moiety) to the exterior surface of the nanoparticle. The additional ligand include or be functionalized to include a chemically reactive functional group which promotes the covalent attachment of the additional ligand to the exterior surface of the nanoparticle. The chemically reactive functional group of the nanoparticle and the chemically reactive functional group of the additional ligand may be selected to be compatible functional groups. For example, the nanoparticle may include a carboxylate, and the additional ligand may include an amine. Methods for conjugating a ligand to a nanoparticle include those disclosed in, e.g., U.S. Pat. Nos. 9,290,617; 9,636,421; and 10,739,349; the methods of attaching ligands to nanoparticles of which are incorporated herein by reference.

EXAMPLES

The following examples are put forth so as to provide those of ordinary skill in the art with a description of how the compositions and methods described herein may be used, made, and evaluated, and are intended to be purely exemplary of the invention and are not intended to limit the scope of the invention.

Example 1: Use of Radiopharmaceuticals

A subject may have a cancerous tumor which is resistant to treatment with conventional cancer therapies. For example, the subject may have pancreatic cancer. The subject may not be eligible for surgical treatment to remove the tumor, for example, due to encasement of the superior mesenteric artery (SMA). The cancer may further be resistant to both external-beam radiation therapy and chemotherapy drugs.

A practitioner may use a radiopharmaceutical composition of the present disclosure to treat the subject. The radiopharmaceutical composition includes a nanoparticle (including or made of, e.g., hyaluronic acid (HA), polyethylene glycol diacrylate (PEGDA), polyglycolic acid (PGA), polylactic acid (PLA), poly(lactic-co-glycolic acid) (PLGA), polysaccharide, polycaprolactone (PCL), collagen, gelatin, poly(methyl methacrylate) (PMMA), polystyrene, carboxymethyl chitosan (CCN), carboxymethyl cellulose (CMC), phospholipids, or a combination thereof), an α-emitting radionuclide, and an imaging agent (e.g., a phospholipid, Feraheme, Gadolinium, Holmium, Europium, Thulium, Cu-64, Tc-99m, In-111, Visipaque, Iohexol or a derivative thereof, or Iohexol related compound B or a derivative thereof) encapsulated by the nanoparticle. The radiopharmaceutical may also include a cell-penetrating ligand (e.g., cell-penetrating ligand is TAT, HSV, gH625, penetratin, VP22, transportan, or a combination thereof) bound to the exterior surface of the nanoparticle. The nanoparticle may further include a complexing moiety (e.g., diethylenetriaminepentaacetate (DTPA), 1,4,7,10-tetraazacyclododecane-1,4,7,10-tetraacetate (DOTA), ethylenediamine tetraacetate (EDTA), cis-1,3,5-cyclohexantriamine (CHTA), triethylene glycol diamine tetraacetate (EGTA), 1,4,8,11-tetraazacyclotetradecane-1,4,8,11-tetraacetate (TETA), 1,4,7,10-tetraazacyclododecane-1,4,7-triacetate (DO3A), 1,4,7-triazacyclononane-1,4,7-triacetate (NOTA), 1,4,7,10,13,16-hexaazacyclooctadecane-1,4,7,10,13,16-hexaacetate (HEHA), N,N'-[(6-carboxy-2-pyridyl(methyl)]-4,13-diaza-18-crown-6 (MACROPA), a reactive derivative thereof, or a combination thereof) bound to the surface of the nanoparticle. The complexing moiety may be bound (e.g., covalently bound) to the nanoparticle at a proximal end (e.g., through an organic moiety configured to bind to the nanoparticle) and an additional chemical component (e.g., a second radionuclide or the cell penetrating ligand) may be bound to a distal end of the complexing moiety (e.g., through an organic moiety configured to bind to the additional chemical component). The radiopharmaceutical may be provided in a kit. The kit may further include components and/or equipment for administering the radiopharmaceutical and/or pharmaceutical composition described herein. An example may be components or equipment that provide vascular access (e.g., a syringe or a vascular access micro puncture set and access sheath).

Each radiopharmaceutical nanoparticle may have a specific activity of from about 0.01 µBq to about 10 µBq. The pharmaceutical composition may have an activity of 0.25 kBq per mL of the pharmaceutical composition. The pharmaceutical composition may have an activity of 0.125 kBq per mL of the target tissue.

The radiopharmaceutical composition thereof may be administered directly into the tumor or proximal to the tumor, without delocalization of the nanoparticle composition throughout the body of the subject (e.g., via the vasculature of the subject). Because of the high energy and low penetration depth of α-emitting radionuclides, the radiopharmaceutical efficiently kills cancerous cells proximal to the injection site, with minimal or no damage to surrounding non-target tissue. A dose of the radiopharmaceutical composition to be delivered may be determined by the amount of radiation desired to be delivered to the target tissue. The desired dose of radiation may be from, e.g., 1 Gy to 100 Gy. A radiopharmaceutical may be administered in one dose or multiple doses.

Administration of the radiopharmaceutical may continue for a treatment duration. The treatment duration may be from about 1 day to about 8 weeks (e.g., 2 days, 3 days, 4 days, 5 days, 6 days, 1 week, 2 weeks, 3 weeks, 4 weeks, 5 weeks, 6 weeks, or 7 weeks). The treatment duration may last until an endpoint of treatment is reached. The endpoint of treatment may be characterized by, e.g., a reduction in tumor size.

During injection of the radiopharmaceutical, and throughout the treatment duration, the response to treatment may be measured by an imaging procedure compatible with the imaging agent. By including an imaging agent in the radiopharmaceutical (e.g., enclosed within the nanoparticle), the imaging agent and the radionuclide stay co-localized, allowing any distribution or change in radionuclide concentration at the target site to be monitored via the imaging procedure.

Other Embodiments

The foregoing detailed description and examples have been given for clarity of understanding only. No unnecessary limitations are to be understood therefrom. The disclosure is not limited to the exact details shown and described, for variations apparent to one skilled in the art will be included within the disclosure defined by the claims.

Unless otherwise indicated, all numbers expressing quantities of components and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications including provisional patent applications, publications including patent publications and non-patent publications, and electronically available material cited herein are incorporated by reference.

The invention claimed is:
1. A radiopharmaceutical comprising:
(a) a plurality of non-encapsulated nanoparticles, each comprising a matrix with an exterior surface;
(b) an imaging agent;
(c) a radionuclide bound to a chelating agent; and
(d) a cell-penetrating ligand;
wherein, for each nanoparticle of the plurality of nanoparticles, the imaging agent and the radionuclide are encapsulated within the nanoparticle and the cell-penetrating ligand is conjugated to the exterior surface of the nanoparticle, wherein each said nanoparticle is from about 1 nm to about 900 nm in diameter, wherein the radiopharmaceutical has a radioactivity of greater than 0.125 kBq per mL, and wherein the cell-penetrating ligand promotes nuclear localization of the nanoparticle.

2. The radiopharmaceutical of claim 1, wherein the matrix of the nanoparticle is a polymer matrix comprising hyaluronic acid (HA), polyethylene glycol diacrylate (PEGDA), polyglycolic acid (PGA), polylactic acid (PLA), poly (lactic-co-glycolic acid) (PLGA), polysaccharide, polycaprolactone (PCL), collagen, gelatin, poly (methyl methacrylate) (PMMA), polystyrene, carboxymethyl chitosan (CCN), carboxymethyl cellulose (CMC), phospholipids, or a combination thereof.

3. The radiopharmaceutical of claim 1, wherein the imaging agent comprises a phospholipid, ferumoxytol, Gadolinium, Holmium, Europium, Thulium, Cu-64, Tc-99m, In-111, Iodixanol, Iohexol or a derivative thereof, Iohexol related compound B or a derivative thereof, or a combination thereof; and wherein the imaging agent is amenable to visualization with an imaging modality selected from the group consisting of ultrasound, fluoroscopy, computed tomography, magnetic resonance imaging, single photon emission computed tomography, positron emission tomography, or a combination thereof.

4. The radiopharmaceutical of claim 1, wherein the radionuclide is a therapeutic radionuclide.

5. The radiopharmaceutical of claim 1, wherein the radionuclide is an α-emitting radionuclide, a β-emitting radionuclide, or an Auger electron emitting radionuclide.

6. The radiopharmaceutical of claim 1, wherein the radionuclide is an α-emitting radionuclide.

7. The radiopharmaceutical of claim 1, wherein the radionuclide undergoes radioactive decay to produce a daughter nucleus, and wherein the daughter nucleus is a therapeutic radionuclide, comprising an α-emitting radionuclide, a β-emitting radionuclide, or an Auger electron emitting radionuclide.

8. The radiopharmaceutical of claim 7, wherein the daughter nucleus comprises an α-emitting radionuclide.

9. The radiopharmaceutical of claim 1, wherein the radionuclide comprises terbium-149, astatine-211, bismuth-212, lead-212, bismuth-213, radium-223, radium-224, actinium-225, thorium-227, yittrium-90, iodine-131, holmium-166, lutetium-177, or a combination thereof.

10. The radiopharmaceutical of claim 1, wherein each said nanoparticle of the plurality of nanoparticles further comprises a complexing moiety bound to the exterior surface of the nanoparticle, wherein the complexing moiety is diethylenetriaminepentaacetate (DTPA), 1,4,7,10-tetraazacyclododecane-1,4,7,10-tetraacetate (DOTA), ethylenediamine tetraacetate (EDTA), cis-1,3,5-cyclohexantriamine (CHTA), triethylene glycol diamine tetraacetate (EGTA), 1,4,8,11-tetraazacyclotetradecane-1,4,8,11-tetraacetate (TETA), 1,4,7,10-tetraazacyclododecane -1,4,7-triacetate (DO3A), 1,4,7-triazacyclononane-1,4,7-triacetate (NOTA), 1,4,7,10,13,16-hexaazacyclooctadecane-1,4,7,10,13,16-hexaacetate (HEHA), N,N'-[(6-carboxy-2-pyridyl (methyl)]-4,13-diaza-18-crown-6 (MACROPA), a reactive derivative thereof, or a combination thereof.

11. The radiopharmaceutical of claim 10, wherein the complexing moiety is conjugated to the nanoparticle through a covalent bond or an ionic bond, wherein optionally, the complexing moiety conjugates the cell-penetrating ligand to the exterior of the nanoparticle.

12. The radiopharmaceutical of claim 1, wherein the cell-penetrating ligand is transactivating transcriptional activator (TAT), herpes simplex virus (HSV), glycoprotein H (gH) domain of herpes simplex virus 1 (gH625), penetratin, VP22, transportan, or a combination thereof.

13. The radiopharmaceutical of claim 1, further comprising a sub-nanoparticle encapsulated within the nanoparticle, wherein the sub-nanoparticle comprises:
(a) a sub-nanoparticle matrix comprising an exterior surface, wherein the sub-nanoparticle matrix comprises a metal matrix or a polymer matrix; and
(b) an imaging agent capable of being visualized with an imaging modality;
wherein the radionuclide of the radiopharmaceutical is localized to the sub-nanoparticle.

14. The radiopharmaceutical of claim 13, wherein the sub-nanoparticle matrix comprises iron, gold, platinum, tantalum, magnetite ($Fe_3O_4$), maghemite ($\gamma$-$Fe_2O_3$), hematite ($\alpha$-$Fe_2O_3$), hyaluronic acid (HA), polyethylene glycol diacrylate (PEGDA), polyglycolic acid (PGA), polylactic acid (PLA), poly (lactic-co-glycolic acid) (PLGA), polysaccharide, polycaprolactone (PCL), Collagen, Gelatin, poly (methyl methacrylate) (PMMA), polystyrene, carboxymethyl chitosan (CCN), carboxymethyl cellulose (CMC), phospholipids, or a combination thereof.

15. The radiopharmaceutical of claim 13, wherein the sub-nanoparticle has a diameter of from about 1 nm to about 10 nm.

16. The radiopharmaceutical of claim 13, wherein the imaging agent of the sub-nanoparticle comprises a phospholipid, ferumoxytol, Gadolinium, Holmium, Europium, Thulium, Cu-64, Tc-99m, In-111, Iodixanol, Iohexol or a derivative thereof, Iohexol related compound B or a derivative thereof, or a combination thereof; and/or the imaging modality for imaging the sub-nanoparticle is ultrasound, fluoroscopy, computed tomography, magnetic resonance imaging, single photon emission computed tomography, positron emission tomography, or a combination thereof.

17. The radiopharmaceutical of claim 13, wherein the sub-nanoparticle further comprises a complexing moiety, wherein the complexing moiety is bound to the exterior surface of the sub-nanoparticle and to a second radionuclide, wherein the complexing moiety of the sub-nanoparticle is a chelator, and wherein the chelator is DTPA, DOTA, EDTA, CHTA, EGTA, TETA, DO3A, NOTA, HEHA, MACROPA, a reactive derivative thereof, or a combination thereof.

18. The radiopharmaceutical of claim 17, wherein the second radionuclide is conjugated to the exterior surface of the sub-nanoparticle via the complexing moiety.

19. The radiopharmaceutical of claim 13, wherein the sub-nanoparticle further comprises a cell-penetrating ligand covalently attached to the exterior surface of the sub-nanoparticle.

20. The radiopharmaceutical of claim 1, wherein each said nanoparticle has a specific activity of about 0.01 µBq to about 10 µBq.

21. A pharmaceutical composition comprising the radiopharmaceutical of claim 1, and a pharmaceutically acceptable excipient.

22. The pharmaceutical composition of claim 21, wherein the excipient is a polyol, a polyether, salcaprozate sodium, or sodium caprate.

23. A kit comprising:
(a) the radiopharmaceutical of claim 1; and
(b) instructions for use thereof, wherein, optionally, the kit further comprises:
(c) a mixer; and/or
(d) a micro puncture set.

24. A method of treating or diagnosing a disease, condition, or disorder in a subject comprising administering the radiopharmaceutical of claim 1 to a subject in need thereof.

25. The method of claim 24, wherein the disease, condition, or disorder comprises neoplastic tissue, a malignancy, or cancer.

26. The method of claim 25, wherein the cancer comprises pancreatic cancer, head and neck cancer, breast cancer, cervical cancer, prostate cancer, retinal cancer, thyroid cancers, lymphomas, meningiomas, brain tumors, or neuroendocrine tumors.

27. The method of claim 24, wherein the radiopharmaceutical or a pharmaceutical composition comprising the radiopharmaceutical is administered into a diseased tissue, wherein the diseased tissue is a solid tumor.

28. The method of claim 27, wherein the radiopharmaceutical or the pharmaceutical composition has a radioactive activity of at least 0.125 kBq per mL of the diseased tissue.

* * * * *